(12) United States Patent
Kouhara et al.

(10) Patent No.: US 6,310,181 B1
(45) Date of Patent: Oct. 30, 2001

(54) ADAPTOR PROTEIN FRS2 AND RELATED PRODUCTS AND METHODS

(75) Inventors: Haruhiko Kouhara, Hyogo (JP); Taly Spivak-Kroizman, Rishon (IL); Irit Lax, Fair Lawn, NJ (US); Joseph Schlessinger, New York, NY (US)

(73) Assignee: New York University Medical Center, New York, NY (US)

( * ) Notice: Subject to any disclaimer, the term of this patent is extended or adjusted under 35 U.S.C. 154(b) by 0 days.

(21) Appl. No.: 08/980,523

(22) Filed: Dec. 1, 1997

Related U.S. Application Data

(60) Provisional application No. 60/032,093, filed on Dec. 3, 1996.

(51) Int. Cl.[7] ................................................. C07K 14/00
(52) U.S. Cl. ......................... 530/350; 530/352; 530/359; 530/358; 435/7.1; 435/183
(58) Field of Search .................. 435/7.1, 183; 530/350, 530/352, 359, 358

(56) References Cited

FOREIGN PATENT DOCUMENTS

| 94/07913 | 4/1994 | (WO) . |
| 95/09365 | 4/1995 | (WO) . |
| 95/24426 | 9/1995 | (WO) . |
| 96/18738 | 6/1996 | (WO) . |
| 96/40115 | 12/1996 | (WO) . |

OTHER PUBLICATIONS

Dietrich, F.S., VAC8 protein–yeast (*Saccharomyces cerevisiae*), Genbank Accession No.: S50446, Feb. 24, 1995.*

Raulf, F., Protein–tyrosine kinase (EC 2.7.1.112)1–freshwater sponge (*Spongilla lacustris*), Genbank Accession No.: S24550, May 7, 1993.*

Abe et al., "Molecular Characterization of a Novel Metabotropic Glutamate Receptor mGluR5 Coupled to Inositol Pohosphate/$Ca^{2+}$ Signal," *J. Biol. Chem.* 267(19):13361–13368 (1992).

Batzer et al., "Hierarchy of binding sites for Grb2 and Shc on the epidermal growth factor receptor," *Mol. Cell. Biol.* 14:5192–5201 (1994).

Bellus et al., "A recurrent mutation in the tyrosine kinase domain of fibroblast growth factor receptor 3 causes hypochondroplasia," *Nature Genetics* 10:357–359 (1995).

Blaikie et al., "A Region in Shc Distinct from the SH2 Domain Can Bind Tyrosine–phosphorylated Growth Factor Receptors," *The Journal of Biological Chemistry* 269(51):32031–32034 (1994).

Clark et al., "*C. elegans* cell–signalling gene sem–5 encodes a protein with SH2 and SH3 domains," *Nature* 356:340–344 (1992).

Curto et al., "Novel Recruitment of Shc, Grb2, and Sos by Fibroblast Growth Factor Receptor–1 in v–Src–Transformed Cells," *Biochemical and Biophysical Research Communications* 243:555–560 (1998).

Deng et al., "Murine FGFR–1 is required for early postimplantation growth and axial organization," *Genes & Dev.* 8:3045–3057 (1994).

DeVore et al., "An FGF receptor signaling pathway is required for the normal cell migrations of the sex myoblasts in *C. elegans* hermaphrodites," *Cell* 83:611–620 (1995).

Dikic et al., "Shc Binding to Nerve Growth Factor Receptor is Mediated by the Phosphotyrosine Interaction Domain," *J. Biol. Chem.* 270:15125–15129 (1995).

Gustafson et al., "Phosphotyrosine–dependent interaction of SHC and insulin receptor substrate 1 with the NPEY motif of the insulin receptor via a novel non–SH2 domain," *Mol. Cell. Biol.* 15:2500–2508 (1995).

Honegger et al., "Point Mutation at the ATP Binding Site of EGF Receptor Abolishes Protein–Tyrosine Kinase Activity and Alters Cellular Routing," *Cell* 51:199–209 (1987).

Jabs et al., "Jackson–Weiss and Crouzon syndromes are allelic with mutations in fibroblast growth factor receptor 2," *Nature Genetics* 8:275–279 (1994).

Klint et al., "Shc and a novel 89–kDa component couple to the Grb–2 Sos complex in fibroblast growth factor–2–stimulated cells," *Journal of Biological Chemistry* 270(40):23337–23344 (1996).

Lowenstein et al., "The SH2 and SH3 Domain–Containing Protein GRB2 Links Receptor Tyrosine Kinases to ras Signaling," *Cell* 70:431–442 (1992).

Mohammadi et al., "Point mutation in FGF receptor eliminates phosphatidylinositol hydrolysis without affecting mitogenesis," *Nature* 358:681–684 (1992).

Muenke et al., "A common mutation in the fibroblast growth factor receptor 1 gene in Pfeiffer syndrome," *Nature Genetics* 8:269–274 (1994).

Nelson, "Detection of Acridinium Esters by Chemiluminescence," *Nonisotopic DNA Probe Techniques,* ed. Larry J. Kricka, (San Diego: Academic Press, Inc.) pp. 275–310 (1992).

Pawson and Schlessinger, "SH2 and SH3 domains," *Current Biology* 3(7):434–442 (1993).

Resh, "Myristylation and palmitylation of Src family members: The fats of the matter," *Cell* 76:411–413 (1994).

(List continued on next page.)

*Primary Examiner*—Rebecca E. Prouty
*Assistant Examiner*—Richard Hutson
(74) *Attorney, Agent, or Firm*—Foley & Lardner

(57) ABSTRACT

The present invention relates generally to a newly identified adaptor protein FRS2 and related products and methods. FRS2 links protein kinases to activating partners in cells. The invention also relates to nucleic acid molecules encoding portions of FRS2, nucleic acid vectors containing FRS2 related nucleic acid molecules, recombinant cells containing such nucleic acid vectors, polypeptides purified from such recombinant cells, antibodies to such polypeptides, and methods of identifying compounds that enhance or block FRS2 interactions with natural binding partners. Also disclosed are methods for diagnosing abnormal conditions in an organism with FRS2 related molecules or compounds.

10 Claims, 1 Drawing Sheet

OTHER PUBLICATIONS

Rozakis–Adcock et al., "Association of the Shc and Grb2/Sem5 SH2–containing proteins is implicated in activation of the Ras pathway by tyrosine kinases," *Nature* 360:689–692 (1992).

Rutland et al., "Identical mutations in the FGFR2 gene cause both Pfeiffer and Crouzon syndrome phenotypes," *Nature Genetics* 9:173–176 (1995).

Sambrook and Maniatis., *Molecular Cloning: A Laboratory Manual*, 2$^{nd}$ Edition, Cold Spring Harbor Laboratory Press (1989) (Table of Contents).

Schlessinger, "SH2/SH3 signaling proteins," *Curr. Opin. Gen. Dev.* 4:25–30 (1994).

Schelssinger et al., "Growth factor signaling by receptor tyrosine kinases," *Neuron* 9:383–391 (1992).

Shiang et al., "Mutations in the transmembrane domain of FGFR3 cause the most common genetic form of dwarfism, achondroplasia," *Cell* 78:335–342 (1994).

Skolnik et al., "The function of GRB2 in linking the insulin receptor to Ras signaling pathways," *Science* 260:1953–1955 (1993).

Spivak–Kroizman et al., "Point mutation in the fibroblast growth factor receptor eliminates phosphatidylinositol hydrolysis without affecting neuronal differentiation of PC12 cells," *J. Biol. Chem.* 269:14419–14423 (1994).

Sun et al., "Structure of the insulin receptor substrate IRS–1 defines a unique signal transduction protein," *Nature* 352:73–77 (1991).

Tavormina et al., "Another mutation that results in the substitution of an unpaired cysteine residue in the extracellular domain of FGFR3 in thanatophoric dysplasia type I," *Hum. Mol. Genetics* 4:2175–2177 (1995).

Vojtek et al., "Mammalian Ras Interacts Directly with the Serine/Threonine Kinase Raf," *Cell* 74:205–214 (1993).

Wang et al., "Broadly expressed SNT–like proteins link FGF receptor stimulation to activators of Ras," *Oncogene* 13:721–729 (1996).

Webster et al., "Constitutive activation of fibroblast growth factor receptor 3 by the transmembrane domain point mutation found in achondroplasia," *EMBO* 15:520–527 (1996).

White et al., "Mutation of the insulin receptor at tyrosine 960 inhibits signal transmission but does not affect its tyrosine kinase activity," *Cell* 54:641–649 (1988).

Yamaguchi et al., "fgfr–1 is required for embryonic growth and mesodermal patterning during mouse gastrulation," *Genes & Dev.* 8:3032–3044 (1994).

* cited by examiner

PTB Domain

```
  1 MGSCCSCPDKDTVPDNHRNKFKVINVDDDGNELGSGVMELTDTELILYTR
 51 KRDSVKWHYLCLRRYGYDSNLFSFESGRRCQTGQGIFAFKCARAEELFNM
101 LQEIMQNNSINVVEEPVVERSSHQTELEVPRTPRTPTTPGLGAQNLPNGY
151 PRYPSFGDASSHPSSRHPSVGSARLPSVGEESTHPLLVAEEQVHTYVNTT
201 GVQEERKNRASVHVPPEARVSNAESNTPKEEPSNPEDRDPQVLLKPEGVR
251 FVLGPTPVQKQLMEKEKLEQLGKDPVSGSGAGNTEWDTGYDSDERRDVPP
301 VNKLVYENINGLSIPSASGVRRGRLTSTSTSDTQNINNSAQRRPALLNYE
351 NLPSLPPVWEARKLSRDEDDNLGPKTPSLNGYHNNLDPMHNYVNTENVTV
401 PASAHKIDYSKRRDCTPTVFNFDIRRPSLEHRQLNYIQVDLEGGSDSDNP
451 QTPKTPTTPLPQTPTRRTELYAVIDIERTAAMSNLQKALPRDDGTSRKTR
501 HNSTDLPM
```

B.

```
                       .β1       .     .β2        β3
IRS-1 148 DTGPGPAFKEVWQVILKPKGLGQTKNLIGIYRLCLTSKTISFVKLNSEAA
              ||.|: . :: :.||    .:::. |:|   : ||...: : ...:
FRS-2  11 DTVPD.NHRNKFKVI....NVDDDGNELGSGVMELTDTELILYTRKRD..
              β4    .β5       β6       . β7         .
IRS-1 198 AVVLQLMNIRRCGHSENFFIEVGRSAVTGPGEFWMQ............
           .| :::.: :||:|...|:|  : :|  ||.| ||.| | :.
FRS-2  54 SVKWHYLCLRRYGYDSNLFSFESGRRCQTGQGIFAFKCARAEELFNMLQE
                         .         .α)          .
IRS-1 235 .........VDDSVVAQNMHETILEAMRAMSDEFRP
                   |::.||...|:| ||. |.... |
FRS-2 104 IMQNNSINVVEEPVVERSSHQTELEVPRTPRTPTTP
```

ADAPTOR PROTEIN FRS2 AND RELATED PRODUCTS AND METHODS

RELATED APPLICATIONS

This application claims the benefit of U.S. patent application Ser. No. 60/032,093, filed Dec. 3, 1996, entitled "Adaptor Protein FRS2 and Related Products and Methods" by Kouhara et al. which is incorporated herein by reference in its entirety, including any drawings.

INTRODUCTION

The present invention relates generally to a newly identified adaptor protein FRS2 and related products and methods. FRS2 links protein kinases to activating partners.

BACKGROUND OF THE INVENTION

The following description of the background of the invention is provided to aid in understanding the invention, but is not admitted to describe or constitute prior art to the invention.

Cellular signal transduction is a fundamental mechanism whereby extracellular stimuli are relayed to the interior of cells and subsequently regulate diverse cellular processes. One of the key biochemical mechanisms of signal transduction involves the reversible phosphorylation of proteins. Phosphorylation of polypeptides regulates the activity of mature proteins by altering their structure and function. Phosphate most often resides on the hydroxyl moiety (—OH) of serine, threonine, or tyrosine amino acids in proteins.

Enzymes that mediate phosphorylation of cellular effectors generally fall into two classes. The first class consists of protein kinases which transfer a phosphate moiety from adenosine triphosphate to protein substrates. The second class consists of protein phosphatases which hydrolyze phosphate moieties from phosphoryl protein substrates. The converse functions of protein kinases and protein phosphatases balance and regulate the flow of signals in signal transduction processes.

Protein kinases are generally divided into two groups—receptor and non-receptor type proteins. Receptor protein kinases straddle the cell membrane and harbor an extracellular region, a transmembrane region, and an intracellular region. Non-receptor protein kinases exist within the cell and harbor a catalytic region attached to other functional regions that can localize the protein kinase to different regions in the cell.

Protein kinases are also typically divided into three classes based upon the amino acids they act upon. Some phosphorylate serine or threonine only, some phosphorylate tyrosine only, and some phosphorylate serine, threonine, and tyrosine.

Many protein kinases, particularly receptor protein kinases, function by binding adaptor proteins. Adaptor proteins link the protein kinase to other proteins that cause a cellular reaction to a protein kinase signal. The epidermal growth factor receptor (EGFR), for example, phosphorylates itself upon binding the EGF ligand. The resulting phosphate moieties on the EGFR intracellular region bind adaptor proteins such as Grb-2. Grb-2 then binds a guanine nucleotide exchange factor protein (Sos), which thereby activates Ras. Ras consequently activates the mitogen activated protein kinase (MAPK) cascade, which causes cellular proliferation or differentiation. Thus, Sos and Ras are direct activating partners of EGFR while members of the MAPK cascade are indirect activating partners of EGFR.

Multiple adaptor proteins harbor domains that directly bind to the phosphate moieties on receptor protein kinase. Grb-2, for example, harbors a Src homology 2 domain (SH2 domain) that tightly binds phosphotyrosine moieties within EGFR and other receptor protein kinases. Pawson and Schlessinger, 1993, *Current Biol.* 3:434–442. Other adaptor proteins, such as IRS-1, can bind phosphotyrosine moieties of receptor protein kinases via a phosphoryl tyrosine binding domain (PTB domain). Gustafson et al., 1995, *Mol. Cell. Biol.* 15:2500–2508. Adaptors such as Shc harbor both SH2 and PTB domains. Blaikie et al., 1994, *J. Biol. Chem.* 269:32031–32034. Some adaptor proteins, such as SNT-like proteins, harbor unidentified phosphotyrosine binding domains because their nucleotide and amino acid sequences are unknown. Wang et al., 1996, *Oncogene* 13:721–729.

It has become evident that receptor protein kinases other than EGFR, such as the fibroblast growth factor receptor protein kinase (FGFR), stimulate the MAPK cascade without directly binding Grb-2. Nakafuku et al., 1992, *J. Biol. Chem.* 267:22963–22966. Scientists are therefore searching for adaptor proteins that link protein kinases to their activating partners to determine the mechanism of activation for these protein kinases. Adaptor proteins involved in protein kinase activation mechanisms are drug targets as compounds that can enhance or abrogate the interactions between the proteins in a protein kinase activation mechanism could potentially prevent and even treat abnormal conditions in organisms caused by altered protein kinase function. Examples of abnormal conditions caused by altered protein kinase function are cancer and other cell proliferative disorders such as arthritis, glomerulonephritis, diabetic nephropathy, malignant nephrosclerosis, thrombotic microangiopathy syndromes, transplant rejection, glomerulopathies, hepatic cirrhosis, ocular diseases such as diabetic retinopathy, and restenosis.

SUMMARY OF THE INVENTION

The present invention relates to nucleic acid molecules encoding a newly identified protein kinase adaptor protein named FRS2. The invention also relates to nucleic acid molecules encoding portions of the full length protein, nucleic acid vectors harboring such nucleic acid molecules, cells containing such nucleic acid vectors, purified polypeptides encoded by such nucleic acid molecules, antibodies to such proteins and polypeptides, and methods of identifying compounds that enhance or block interactions of FRS2 with natural binding partners. Also disclosed are methods for diagnosing abnormal conditions in an organism with FRS2 related molecules or compounds. The nucleic acid molecules, nucleic acid vectors, host cells, polypeptides, and antibodies may be produced using the information provided herein in conjunction with well known and standard techniques used currently in the art.

FRS2 (Fibroblast Growth Factor Receptor Protein Kinase substrate 2) regulates growth factor stimulation of cellular differentiation and cellular proliferation by linking stimulated fibroblast growth factor receptor (FGFR) to the Ras/MAPK cascade via the Grb-2/Sos complex. Various treatments of cell proliferative disorders and cell differentiation disorders are therefore provided based on the discovery of FRS2.

The FRS2 adaptor protein of the invention is isolated from human NIH 3T3 cells. The invention also relates to closely related adaptor proteins preferably from mammalian tissue and more preferably from human tissue. The term "closely related" refers to greater than 50% amino acid identity or a similar three dimensional structure. The term "amino acid identity" is described herein.

Thus in a first aspect, the invention features an isolated, enriched, or purified nucleic acid molecule encoding a FRS2 polypeptide.

The term "isolated", in reference to nucleic acid molecules, indicates that a naturally occurring sequence has been removed from its normal cellular environment. Thus, the sequence may be in a cell-free solution or placed in a different cellular environment. The term does not imply that the sequence is the only nucleotide chain present, but that it is essentially free (about 90–95% pure at least) of non-nucleotide material such as chromosomal DNA or proteins.

The term "enriched", in reference to nucleic acid molecules, means that the specific DNA or RNA sequence constitutes a significantly higher fraction (2–5 fold) of the total DNA or RNA present in the cells or solution of interest than in normal or diseased cells or in the cells from which the sequence was taken. A person skilled in the art could enrich a nucleic acid mixture by preferentially reducing the amount of other DNA or RNA present, or preferentially increasing the amount of the specific DNA or RNA, or both. However, nucleic acid molecule enrichment does not imply that there is no other DNA or RNA present, the term only indicates that the relative amount of the sequence of interest has been significantly increased. The term "significantly" qualifies "increased" to indicate that the level of increase is useful to the person performing the recombinant DNA technique, and generally means an increase relative to other nucleic acids of at least 2 fold, or more preferably at least 5 to 10 fold or more. The term also does not imply that there is no DNA or RNA from other sources. Other DNA may, for example, comprise DNA from a yeast or bacterial genome, or a cloning vector. In addition, levels of mRNA may be naturally increased relative to other species of mRNA when working with viral infection or tumor growth techniques. The term "enriched" is meant to cover only those situations in which a person has intervened to elevate the proportion of the desired nucleic acid.

Many methods of recombinant nucleic acid manipulation require that these molecules are in a purified form. The term "purified", in reference to nucleic acid molecules does not require absolute purity (such as a homogeneous preparation); instead, it represents an indication that the sequence is relatively more pure than in its cellular environment (compared to the natural level this level should be at least 2–5 fold greater, e.g., in terms of mg/ml). The claimed DNA molecules obtained from clones could be obtained directly from total DNA or from total RNA. cDNA clones are not naturally occurring, but rather are preferably obtained via manipulation of a partially purified, naturally occurring substance (messenger RNA). The construction of a cDNA library from mRNA involves the creation of a synthetic substance (cDNA). Individual cDNA clones can be isolated from the synthetic library by clonal selection of the cells carrying the cDNA library. Thus, the process which includes the construction of a cDNA library from mRNA and isolation of distinct cDNA clones yields an approximately $10^6$-fold purification of the native message. Thus, purification of at least one order of magnitude, preferably two or three orders, and more preferably four or five orders of magnitude is favored in these techniques.

The term "nucleic acid molecule" describes a polymer of deoxyribonucleotides (DNA) or ribonucleotides (RNA). The nucleic acid molecule may be isolated from a natural source by cDNA cloning or subtractive hybridization or synthesized manually. The nucleic acid molecule may be synthesized manually by the triester synthetic method or by using an automated DNA synthesizer.

The term "cDNA cloning" refers to hybridizing a small nucleic acid molecule, a probe, to genomic cDNA that is bound to a membrane. The probe hybridizes (binds) to complementary sequences of cDNA.

The term "complementary" describes two nucleotides that can form multiple favorable interactions with one another. For example, adenine is complementary to thymidine as they can form two hydrogen bonds. Similarly, guanine and cytosine are complementary since they can form three hydrogen bonds. Thus a "complement" of a nucleic acid molecule is a molecule containing adenine instead of thymine, thymine instead of adenine, cytosine instead guanine, and guanine instead of cytosine. Because the complement contains a nucleic acid sequence that forms optimal interactions with the parent nucleic acid molecule, such a complement binds with high affinity to its parent molecule.

The term "hybridize" refers to a method of interacting a nucleic acid probe with a DNA or RNA molecule in solution or on a solid support, such as cellulose or nitrocellulose. If a nucleic acid probe binds to the DNA or RNA molecule with high affinity, it is said to "hybridize" to the DNA or RNA molecule. As mentioned above, the strength of the interaction between the probe and its target can be assessed by varying the stringency of the hybridization conditions. Various low or high stringency hybridization conditions may be used depending upon the specificity and selectivity desired. Stringency is controlled by varying salt or denaturant concentrations. Under stringent hybridization conditions only highly complementary nucleic acid sequences hybridize. Preferably, such conditions prevent hybridization of nucleic acids having one or two mismatches out of 20 contiguous nucleotides.

cDNAs are molecules that may be reverse-transcribed from fragments of message RNA from a genomic source. These fragments form a cDNA library of nucleic acid molecules. cDNA libraries are constructed from natural sources such as mammalian blood, semen, or tissue.

The term "subtractive hybridization" refers to a method similar to cDNA cloning except that cDNA prepared from mRNA in unstimulated cells is added to mRNA in stimulated or different types of cells. cDNA/mRNA can then be precipitated to enrich the mRNA specific to the stimulation signal or different cell type.

The term "FRS2 polypeptide" refers to a polypeptide having an amino acid sequence preferably of at least 400 contiguous amino acids, more preferably of at least 450 contiguous amino acids, or most preferably of at least 508 contiguous amino acids set forth in FIG. 1A, or is substantially similar to such a sequence. A sequence that is substantially similar will preferably have at least 90% identity (more preferably at least 95% and most preferably 99–100%) identity to the amino acid sequence of FIG. 1A. FRS2 polypeptides preferably have Grb-2 binding activity and fragments of the full length FRS2 sequence having such activity may be identified using techniques well known in the art, such as sequence comparisons and assays such as those described in the examples herein.

"Identity" refers to a property of sequences that measures their similarity or relationship. Identity is measured by dividing the number of identical residues by the total number of residues and multiplying the product by 100. Thus, two copies of exactly the same sequence have 100% identity, but sequences that are less highly conserved and have deletions, additions, or replacements may have a lower degree of identity. Those skilled in the art will recognize that several computer programs are available for determining sequence identity. Such programs are generally able to achieve maximum alignment by ignoring deletions or additions that would otherwise alter the calculation of the percentage of identity between two sequences.

A preferred embodiment concerns nucleic acid molecules relating to FRS2 enriched, isolated, or purified from a mammalian source. These nucleic acid molecules can be isolated from, among other sources, blood, semen, or tissue.

The term "mammalian" refers to such organisms as mice, rats, rabbits, goats, preferably monkeys and apes, and more preferably humans. Although the FRS2 nucleic acid molecule of FIG. 1A is isolated from NIH 3T3 cells, current recombinant DNA techniques can readily elucidate a related nucleic acid molecule in other tissues.

Another preferred embodiment concerns an isolated nucleic acid molecule relating to FRS2 that encodes at least twelve contiguous amino acids of the amino acid sequence set forth in FIG. 1A. Preferably at least 3, 5, 10, 15, 20, 25, 30, 35, 40, 50, 100, 200, 300, 400, 500 or 508 contiguous amino acids of the FRS2 sequence are encoded. This preferred embodiment of the invention is achieved by applying routine recombinant DNA techniques known to those skilled in the art.

Another aspect of the invention features a nucleic acid probe that can detect nucleic acid molecules encoding a FRS2 polypeptide in a sample.

The term "nucleic acid probe" refers to a nucleic acid molecule that is complementary to and can bind a nucleic acid sequence encoding the amino acid sequence substantially similar to that set forth in FIG. 1A.

The nucleic acid probe or its complement encodes any one of the amino acid molecules set forth in the invention. Thus the nucleic acid probe can encode at least 3, 5, 10, 15, 20, 25, 30, 35, 40, 50, 100, 200, 300, 400, 500 or 508 contiguous amino acids of the full-length sequence set forth in FIG. 1A.

The nucleic acid probe can be labeled with a reporter molecule or molecules. The term "reporter molecule" refers to a molecule that is conjugated to the nucleic acid probe or is contained within the nucleic acid probe. The reporter molecule allows the detection of the probe by methods used in the art. Reporter molecules are chosen from, but limited to, the group consisting of an enzyme, such as a peroxidase, a radioactive element, or an avidin molecule.

A nucleic acid probe, whether labeled or unlabeled, should hybridize to a complement in a sample.

The nucleic acid probe can be a nucleic acid molecule encoding a conserved or unique region of amino acids. These nucleic acid molecules are useful as hybridization probes to identify and clone additional polypeptides relating to FRS2.

The term "conserved nucleic acid regions", refers to regions present in two or more nucleic acid molecules encoding a FRS2 polypeptide, to which a particular nucleic acid sequence can hybridize under lower stringency conditions. Examples of lower stringency conditions suitable for screening nucleic acid molecules are provided in Abe, et al. *J. Biol. Chem.* 19:13361 (1992) (hereby incorporated by reference herein in its entirety, including any drawings). Preferably, conserved regions differ by no more than 5 out of 20 nucleotides. As mentioned above, protein tyrosine kinases share conserved regions in their extracellular and catalytic domains.

The term "unique nucleic acid region" concerns a sequence present in a full length nucleic acid coding for a FRS2 polypeptide that is not present in a sequence coding for any other naturally occurring polypeptide. Such regions preferably comprise 30 or 45 contiguous nucleotides present in the full length nucleic acid sequence encoding a FRS2 polypeptide. In particular, a unique nucleic acid region is preferably of mammalian origin.

Methods for using the probes include detecting the presence or amount of FRS2 RNA in a sample by contacting the sample with a nucleic acid probe under conditions such that hybridization occurs. The nucleic acid duplex formed between the probe and a nucleic acid sequence coding for a FRS2 polypeptide may be used in the identification of the sequence of the nucleic acid detected (for example see, Nelson et al., in *Nonisotopic DNA Probe Techniques,* p. 275 Academic Press, San Diego (Kricka, ed., 1992) hereby incorporated by reference herein in its entirety, including any drawings). Kits for performing such methods may be constructed to include a container holding a nucleic acid probe.

In yet another aspect, the invention relates to a nucleic acid vector comprising a nucleic acid molecule encoding a FRS2 polypeptide and a promoter element effective to initiate transcription in a host cell.

The term "nucleic acid vector" relates to a single or double stranded circular nucleic acid molecule that can be transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that the restriction enzymes operate upon are readily available to those skilled in the art. A nucleic acid molecule of the invention can be inserted into a vector by cutting the vector with restriction enzymes and ligating the two pieces together.

Many techniques are available to those skilled in the art to facilitate transformation or transfection of the expression construct into a prokaryotic or eukaryotic organism. Sambrook, Fritsch, Maniatis, 1989, "Molecular Cloning", Cold Spring Harbor Laboratory Press, United States. The terms "transformation" and "transfection" refer to methods of inserting an expression construct into a cellular organism. These methods involve a variety of techniques, such as treating the cells with high concentrations of salt, an electric field, or detergent, to render the host cell outer membrane or wall permeable to nucleic acid molecules of interest.

The term "promoter element" describes a nucleotide sequence that is incorporated into a vector that, once inside an appropriate cell, can facilitate transcription factor and/or polymerase binding and subsequent transcription of portions of the vector DNA into mRNA. The promoter element precedes the 5' end of the FRS2 nucleic acid molecule such that the latter is transcribed into mRNA. Host cell machinery then translates mRNA into a polypeptide.

Those skilled in the art would recognize that a nucleic acid vector can contain many other nucleic acid elements besides the promoter element and the FRS2 nucleic acid molecule. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, periplasm or peroxisome localization signals, or signals useful for polypeptide purification.

A nucleic acid vector can be useful for identifying natural binding partners of FRS2 polypeptides.

The term "natural binding partners" refers to polypeptides that bind to FRS2 and play a role in propagating a signal in a signal transduction process. The term "binding partner" also refers to a polypeptide that binds to FRS2 within a cellular environment with high affinity. High affinity represents an equilibrium binding constant on the order of $10^{-6}$ M. However, a natural binding partner can also transiently interact with a FRS2 polypeptide and chemically modify it. FRS2 natural binding partners are chosen from a group consisting of, but not limited to, src homology 2 (SH2) or 3 (SH3) domains, other phosphoryl tyrosine binding domains (PTB and PH domains), guanine nucleotide exchange factors, and receptor and non-receptor protein kinases or protein phosphatases. A known natural binding partner of FRS2 is the SH2 containing Grb-2.

Methods are readily available in the art for identifying natural binding partners of polypeptides of interest by screening cDNA libraries included in one nucleic acid vector with a nucleic acid molecule encoding the desired polypeptide in another expression construct. Vojtek et al., 1993, Cell 74:205–214. These techniques often utilize two halves of a transcription factor, one of which is fused to a polypeptide encoded by the cDNA library, and the other or which is fused to the polypeptide of interest. Interactions between a polypeptide encoded by the cDNA library and the polypeptide of interest are detected when their interaction concomitantly brings together the two halves of the transcription factor and activates a gene that reports the interaction. Any of the nucleic molecules encoding FRS2 polypeptide can be readily incorporated into a nucleic acid vector used in such a screening procedure by utilizing standard recombinant DNA techniques in the art.

Another aspect of the invention relates to a recombinant cell or tissue comprising a nucleic acid molecule encoding a FRS2 polypeptide.

The term "recombinant" refers to an organism that has a new combination of genes or nucleic acid molecules. A new combination of genes or nucleic acid molecules can be introduced to an organism using a wide array of nucleic acid manipulation techniques available to those skilled in the art.

The recombinant cell can be a eukaryotic or prokaryotic organism.

The term "eukaryote" refers to an organism comprised of cells that contain a nucleus. Eukaryotes are differentiated from "prokaryotes" which do not house their genomic DNA inside a nucleus. Prokaryotes include unicellular organisms such as bacteria while eukaryotes are represented by yeast, invertebrates, and vertebrates.

The term "organism" relates to any living being comprised of at least one cell. An organism can be as simple as one eukaryotic cell or as complex as a mammal.

The recombinant cell can harbor a nucleic acid vector that is extragenomic. The term "extragenomic" refers to a nucleic acid vector which does not insert into the cell genome. Many nucleic acid vectors are designed with their own origins of replication allowing them to utilize the recombinant cell replication machinery to copy and propagate the vector nucleic acid sequence. These vectors are small enough that they are not likely to harbor nucleic acid sequences homologous to genomic sequences of the recombinant cell. Thus these vectors replicate independently of the host genome and do not recombine with or integrate into the genome.

A recombinant cell can harbor a portion of a nucleic acid vector in an intragenomic fashion. The term "intragenomic" defines a nucleic acid construct that is incorporated within the cell genome. Multiple nucleic acid vectors available to those skilled in the art contain nucleic acid sequences that are homologous to nucleic acid sequences in a particular organism's genomic DNA. These homologous sequences will result in recombination events that integrate portions of the vector into the genomic DNA. Those skilled in the art can control which nucleic acid sequences of the vector are integrated into the cell genome by flanking the portion to be incorporated into the genome with homologous sequences in the vector.

Yet another aspect of the invention features an isolated, enriched, or purified FRS2 polypeptide.

The term "isolated", in reference to a polypeptide, describes a polymer of amino acids conjugated to one other, including polypeptides that are isolated from a natural source or that are synthesized. In certain aspects longer polypeptides are preferred, such as those with most of the contiguous amino acids set forth in FIG. 1A.

The isolated polypeptides of the present invention are unique in the sense that they are not found in a pure or separated state in nature. Use of the term "isolated" indicates that a naturally occurring sequence has been removed from its normal cellular environment. Thus, the sequence may be in a cell-free solution or placed in a different cellular environment. The term does not imply that the sequence is the only amino acid chain present, but that it is essentially free (about 90–95% pure at least) of non-amino acid material naturally associated with it.

The term "enriched", in reference to a polypeptide, defines a specific amino acid sequence constituting a significantly higher fraction (2–5 fold) of the total of amino acids present in the cells or solution of interest than in normal or diseased cells or in the cells from which the sequence was separated. A person skilled in the art can preferentially reduce the amount of other amino acid sequences present, or preferentially increase the amount of specific amino acid sequences of interest, or both. However, the term "enriched" does not imply that there are no other amino acid sequences present. Enriched simply means the relative amount of the sequence of interest has been significantly increased. The term "significant" indicates that the level of increase is useful to the person making such an increase. The term also means an increase relative to other amino acids of at least 2 fold, or more preferably at least 5 to 10 fold, or even more. The term also does not imply that there are no amino acid sequences from other sources. Other source amino acid sequences may, for example, comprise amino acid sequences from a host organism. "Enriched" is meant to cover only those situations in which a person has intervened to elevate the proportion of the desired amino acid sequence.

The term "purified", in reference to a polypeptide, does not require absolute purity (such as a homogeneous preparation); instead, it represents an indication that the amino acid sequence is relatively more pure than in a cellular environment. The concentration of the preferred amino acid sequence should be at least 2–5 fold greater (in terms of mg/ml) than its concentration in a cellular environment. Purification of at least one order of magnitude, preferably two or three orders, and more preferably four or five orders of magnitude is preferred. The substance is preferably free of contamination, as indicated by purity levels of 90%, 95%, or 99%.

A preferred embodiment relates to a FRS2 polypeptide that is a unique fragment of a FRS2 polypeptide.

The term "unique fragment" refers to a stretch of contiguous amino acids in FRS2 that is of a different sequence than another adaptor protein. From the sequence alignment between FRS2 and a closely related region of the adaptor protein IRS-1 indicates that the two sequences share only two contiguous amino acids. Therefore at least 3, 5, 10, 15, 20, 25, 30, 35, 40, 50, 100, 200, 300, 400, 500 or 508 contiguous amino acids of the full-length amino acid sequence of FRS2 are unique to FRS2.

The FRS2 polypeptide can be isolated, enriched, or purified from a prokaryotic or eukaryotic recombinant cell. A eukaryotic cell can arise from organisms including mammals. Multiple standard techniques are available to those skilled in the art to facilitate isolation, enrichment, or purification of a polypeptide from recombinant cells. These methods typically include lysing the recombinant cells and separating the polypeptide of interest from the rest of the cell polypeptides, nucleic acids, and fatty acid-based material using standard chromatography techniques known in the art.

In the context of the present invention, isolation, enrichment, or purification of polypeptides is attained by techniques that provide yields of FRS2 that can be visualized on a nitrocellulose membrane by Ponceau-S staining or can be visualized on a sodium dodecyl sulfate polyacrylamide gel by Coomassie or silver staining.

Another aspect of the invention features an antibody, that is monoclonal or polyclonal, or an antibody fragment having specific binding affinity to a FRS2 polypeptide.

Antibodies or antibody fragments are polypeptides which contain regions that can bind other polypeptides. The term "specific binding affinity" describes an antibody that binds to a FRS2 polypeptide with greater affinity than it binds to other polypeptides under specified conditions.

The term "polyclonal" refers to a mixture of antibodies with specific binding affinity to a FRS2 polypeptide, while the term "monoclonal" refers to one type of antibody with specific binding affinity to a FRS2 polypeptide. Although a monoclonal antibody binds to one specific region on a FRS2 polypeptide, a polyclonal mixture of antibodies can bind multiple regions of a FRS2 polypeptide.

The term "antibody fragment" refers to a portion of an antibody, often the hypervariable region and portions of the surrounding heavy and light chains, that displays specific binding affinity for a particular molecule. A hypervariable region is a portion of an antibody that physically binds to the polypeptide target.

Antibodies or antibody fragments having specific binding affinity to a FRS2 polypeptide may be used in methods for detecting the presence and/or amount of a FRS2 polypeptide in a sample by probing the sample with the antibody under conditions suitable for FRS2-antibody immunocomplex formation and detecting the presence and/or amount of the antibody conjugated to the FRS2 polypeptide. Diagnostic kits for performing such methods may be constructed to include antibodies or antibody fragments specific for FRS2 as well as a conjugate of a binding partner of the antibodies or the antibodies themselves.

An antibody or antibody fragment with specific binding affinity to a FRS2 polypeptide can be isolated, enriched, or purified from a prokaryotic or eukaryotic organism. Routine methods known to those skilled in the art enable production of antibodies or antibody fragments, in both prokaryotic and eukaryotic organisms. Purification, enrichment, and isolation of antibodies, which are polypeptide molecules, are described above.

Another aspect of the invention features a hybridoma which produces an antibody having specific binding affinity to a FRS2 polypeptide. A "hybridoma" is an immortalized cell line which is capable of secreting an antibody, for example an antibody with specific binding affinity to FRS2.

Another aspect of the invention features an isolated, enriched, or purified nucleic acid molecule comprising a nucleotide sequence that: (a) encodes a polypeptide having the full length amino acid sequence set forth FIG. 1A; (b) the complement of the nucleotide sequence of (a); (c) hybridizes under highly stringent conditions to the nucleotide molecule of (a) and encodes a naturally occurring FRS2 protein; (d) a FRS2 polypeptide having the full length amino acid sequence of sequence set forth in FIG. 1A except that it lacks one or more of the following segments of amino acid residues 1–10, 11–152, or 153–508; (e) the complement of the nucleic acid sequence of (d); (f) a polypeptide having the amino acid sequence set forth in FIG. 1A from amino acid residues 1–10, 11–152, 153–508; (g) the complement of the nucleic acid sequence of (f); (h) encodes a polypeptide having the full length amino acid sequence set forth in FIG. 1A except that it lacks one or more of the domains selected from the group consisting of a myristylation region, a phosphotyrosine binding region, and a C-terminal region; (i) the complement of the nucleic acid sequence of (h); (j) encodes a polypeptide of (a), (d), or (f) containing one or both of the mutations tyrosine 349 to phenylalanine or tyrosine 392 to phenylalanine; or (k) the complement of the nucleic acid sequence of (j).

The term "myristylation region" refers to a portion of the full length FRS2 amino acid sequence that harbors a myristoyl fatty acid moiety. This region preferably spans from the amino acids 1 through 10.

The term "phosphotyrosine binding region" refers to a portion of the FRS2 amino acid molecule that can bind to a phosphotyrosine moiety within another protein or polypeptide. This region preferably spans from amino acids 11 through 152.

The term "C-terminal domain" refers to a portion of FRS2 that begins at the end of the phosphotyrosine binding region to the carboxy terminal end of FRS2. This region preferably spans from amino acids 153 to 508.

Functional regions of FRS2 may be identified by aligning the amino acid sequence of FRS2 with amino acid sequences of other polypeptides with known functional regions. If regions of FRS2 share high amino acid identity with the amino acid sequences of known functional regions, then FRS2 can be determined to contain these functional regions by those skilled in the art. The functional regions can be determined, for example, by using computer programs and sequence information available to those skilled in the art.

Other functional regions of signal transduction molecules that may exist in the FRS2 amino acid sequence include, but are not limited to, proline-rich regions or phosphoryl tyrosine regions. These regions can interact with natural binding partners such as SH2 or SH3 domains of other signal transduction molecules. Examples of two potential SH2 binding regions of FRS2 are tyrosine 349 and 392. If these tyrosines are phosphorylated in the cell, SH2 containing proteins, such as Grb-2, can bind FRS2 at these sites. Mutating these tyrosines to phenylalanine will abrogate the binding of any SH2 containing proteins at these mutated sites.

In yet another aspect, the invention includes a nucleic acid vector containing a nucleic acid molecule described above.

Another aspect of the invention relates to a recombinant cell or tissue that contains a nucleic acid molecule described above.

In yet another aspect, the invention features a method of identifying compounds capable of blocking or enhancing interactions between FRS2 and natural binding partners. These compounds are potentially useful for diagnosing, preventing, or treating abnormal conditions in an organism. The method consists of the following steps: (a) adding a compound to cells containing a FRS2 polypeptide; and (b) detecting a change in interactions between FRS2 and natural binding partners.

The term "compound" includes small organic molecules including, but not limited to, oxindolinones, quinazolines, tyrphostins, quinoxalines, and extracts from natural sources.

The term "interactions" refers to FRS2 binding to natural binding partners. The invention discloses that FRS2 binds to Grb-2. Thus interactions are formed between FRS2 amino acids and the amino acids of Grb-2. An interaction between two molecules preferably relates to the two molecules binding to one another and forming a complex.

The term "blocking interactions" refers to decreasing the concentration of a complex formed between two molecules. The decrease in the concentration of the complex can be achieved by decreasing the probability that the two molecules form a complex by binding a compound to one of them. A compound that binds with high affinity to one of the molecules in the complex can decrease the probability that a complex forms between the molecules if the compound decreases the likelihood that amino acids between the two molecules can form favorable interactions with one another.

The term "enhancing interactions" refers to increasing the concentration of a complex formed between two molecules. The increase in the concentration of the complex can be achieved by increasing the probability that the two molecules form a complex by binding a compound to one of them. A compound that binds with high affinity to one of the molecules in the complex can increase the probability that a complex forms between the molecules if the compound increases the likelihood that amino acids between the two molecules can form favorable interactions with one another.

The term "abnormal condition" refers to a function in an organism's cells or tissue that deviate from a normal function in the cells or tissue of that organism. In the context of the invention, an abnormal condition is associated with an aberration in a signal transduction pathway involving FRS2. Abnormal conditions can be associated with cell proliferation. Cell proliferative disorders include cancers such as fibrotic and mesangial disorders, abnormal angiogenesis and vasculogenesis, slow wound healing rates, psoriasis, diabetes mellitus, and inflammation. Abnormal conditions can also be associated with cell differentiation. Cell differentiation disorders include, but are not limited to neurodegenerative disorders, slow wound healing rates, and slow tissue grafting healing rates.

The abnormal condition can be diagnosed, prevented, or treated when the organism's cells exist within the organism or outside of the organism. Cells existing outside the organism can be maintained or grown in cell culture dishes. For cells harbored within the organism, many techniques exist in the art to administer compounds, including (but not limited to) oral, parenteral, dermal, and injection applications. For cells outside of the patient, multiple techniques exist in the art to administer the compounds, including (but not limited to) cell microinjection techniques, transformation techniques, and carrier techniques.

The term "signal transduction pathway" refers to the molecules that propagate an extracellular signal through the cell membrane to become an intracellular signal. This signal can then stimulate a cellular response. The polypeptide molecules involved in signal transduction processes are typically receptor and non-receptor protein kinases, receptor and non-receptor protein phosphatases, and transcription factors.

The term "aberration", in conjunction with a signal transduction process, refers to a FRS2 protein or other protein involved in a signal transduction pathway involving FRS2 that is over- or under-expressed in an organism, mutated such that its catalytic activity is lower or higher than the wild-type molecule, mutated such that it can no longer interact with a binding partner, is no longer modified by another protein kinase or protein phosphatase, or no longer interacts with a binding partner.

The term "detecting a change in interactions", in the context of the invention, defines a method of determining whether a compound enhances or blocks the interaction between FRS2 and natural binding partners. Multiple methods exist within the art that can detect a complex formed between FRS2 and natural binding partners. One such method is disclosed herein by example in relation to the interaction formed between FRS2 and Grb-2.

The interaction between FRS2 and natural binding partners can also be detected by a difference in a cell morphology. Differences in cell morphology include growth rates and differentiation rates of cells. These phenomena are simply measured by methods in the art. These methods typically involve observing the number of cells or the appearance of cells under a microscope with respect to time (days).

The method can utilize any of the molecules disclosed in the invention. These molecules include nucleic acid molecules encoding FRS2 polypeptides, nucleic acid vectors, recombinant cells, polypeptides, or antibodies of the invention.

The method can be performed in vitro as well as in vivo. In vivo applications include introducing a group of cells to an organism and then determining the effect of a compound administered to the organism on the state of the organism as well as the introduced cells. The art contains multiple methods of introducing a group of cells to an organism as well as methods of administering a compounds to an organism. The organism is preferably an animal such as a frog, more preferably a mouse, rat, or rabbit, and most preferably a monkey, ape, or human.

Another aspect of the invention relates to a method of diagnosing an abnormal condition associated with cell proliferation or cell differentiation in an organism. The abnormal condition can be associated with an aberration in a signal transduction pathway characterized by an interaction between a FRS2 polypeptide and a natural binding partner. The method comprises of the step of detecting an abnormal interaction.

The term "detecting an abnormal interaction" defines a method of identifying a FRS2 molecule with an aberration in its activity. Detection is accomplished by using an antibody or antibody fragment of the invention, a nucleic acid probe of the invention, or a compound of the invention.

Techniques used in the art that incorporate this method include in vitro, in vivo, and in situ hybridization techniques. These techniques utilize nucleic acid probes of the invention.

A preferred embodiment of the invention is that the diagnosis method relates to an organism that is a mammal.

The summary of the invention described above is not limiting and other features and advantages of the invention will be apparent from the following detailed description of the invention, and from the claims.

BRIEF DESCRIPTION OF THE FIGURE

FIG. 1A is the amino acid sequence of the FRS2 protein isolated from NIH 3T3 cells. Four tryptic peptides are underlined in the amino acid sequence. The myristylation sequence is underlined with a hatched line at the N-terminus. The portion of the FRS2 protein corresponding to the phosphotyrosine binding domain (PTB domain) is boxed in the figure. Putative SH2 binding regions of FRS2 are indicated in bold.

FIG. 1B aligns the sequence of the PTB domain of another adaptor protein, IRS-1, with that of FRS2. Secondary structural elements (including α-helices and β-sheets) are boxed. Vertical lines report identical amino acids shared between the two proteins. Only two contiguous amino acids are identical within the two proteins.

DETAILED DESCRIPTION OF THE INVENTION

The present invention is based in part upon the isolation and characterization of nucleic acid molecules encoding an adaptor protein designated FRS2 that links protein kinases to activating proteins in cells. The invention also relates to nucleic acid molecules encoding portions of the FRS2 polypeptide, nucleic acid molecules encoding at least one FRS2 functional portion, nucleic acid vectors harboring such nucleic acid molecules, recombinant cells containing such nucleic acid vectors, purified polypeptides encoded by such nucleic acid molecules, antibodies to such polypeptides, and methods of identifying compounds that enhance or block interactions of FRS2 with natural binding partners. Also disclosed are methods for diagnosing abnormal conditions in an organism with FRS2 related molecules or compounds.

Experiments reported herein by example suggest that FRS2 links FGFR to the activating Ras/MAPK pathway via Grb-2/Sos. Observations in the literature underscore the importance of the FGFR-FRS2 interaction as alterations in FGFR function lead to diseased states in organisms.

A number of mutations in FGFR1 and FGFR2 lead to severe craniofacial abnormalities and characteristic abnormalities in the foot, thumb and toes. These mutations are responsible for Pfeiffer, Jackson-Weiss and Crouzon syndromes (Muenke et al., 1994, Nature Genetics 8:269–274; Jabs et al., 1994, Nature Genetics 8:275–279; Rutland et al., 1995, Nature Genetics 9:173–176). Experiments with mice genetically deficient in FGFR1 have confirmed the central role of this receptor in embryonic growth and axial gastrulation (Yamaguchi et al., 1994, Genes&Dev. 8:3032–3044; Deng et al., 1994, Genes&Dev. 8:3045–3057).

Mutations have also been identified in FGFR3 that lead to skeletal dysplasias and hypochondroplasia (Tavormina et al., 1995, Hum. Mol. Genetics 4:2175–2177; Bellus et al., 1995, Nature Genetics 10:357–359). One mutation in FGFR3 is responsible for the most common form of human dwarfism (Shiang et al., 1994, Cell 78:335–342), apparently resulting from a gain-of-function mutation that leads to constitutive activation of the intrinsic protein kinase activity of the FGF receptor (Webster and Donoghue, 1996, EMBO 15:520–527). Inactivation of the FGFR3 gene in mice causes severe bone dysplasia with enhanced bone growth (Deng et al., 1996, Genes&Dev. 8:3045–3057).

Loss of function mutations identified in the *C. elegans* homologue of the FGF receptor also lead to severe developmental disorders (DeVore et al., 1995, Cell 83:611–620). Therefore, FRS2 is a drug design target for these diseases. In addition, FRS2 is a drug design target for other abnormal conditions in organisms since FGFR is an important regulatory molecule in cell proliferation and differentiation pathways.

Various other features and aspects of the invention are: nucleic acid molecules encoding a FRS2 polypeptide; recombinant DNA techniques to manipulate nucleic acid molecules; nucleic acid probes for the detection of FRS2; a probe-based method and kit for detecting FRS2 messages in other organisms; DNA constructs comprising a FRS2 nucleic acid molecule and cells containing these constructs; methods of isolating, enriching or purifying FRS2 polypeptides; FRS2 antibodies and hybridomas; antibody-based methods and kits for detecting FRS2; identification of agents; isolation of compounds which interact with a FRS2 polypeptide; compositions of compounds that interact with FRS2 and FRS2 molecules; preparation of pharmaceutical formulations of compounds; modes of administration of compounds to organisms; purification and production of complexes; derivatives of complexes; antibodies to complexes; disruption of FRS2 protein complexes; transgenic animals containing FRS2 nucleic acid constructs; antisense and ribozyme approaches, gene therapy; and evaluation of disorders. Those skilled in the art appreciate that any modifications made to a complex can be manifested in the modification of any of the molecules in that complex. Thus, the invention includes any modifications to nucleic acid molecules, polypeptides, antibodies, or compounds in a complex. All of these aspects and features are explained in detail with respect to PYK-2 in PCT publication WO 96/18738, which is incorporated herein by reference in its entirety, including any drawings. Those skilled in the art will readily appreciate that such descriptions can be easily adapted to FRS2 as well, and is equally applicable to the present invention.

EXAMPLES

The examples below are non-limiting and are merely representative of various aspects and features of the present invention. The examples below demonstrate the isolation, and characterization of the novel protein FRS2. Materials and methods utilized in the experiments disclosed in the examples are as follows:

Cell lines: PC12 cells (Spivak-Kroizman et al., 1994, J. Biol. Chem. 269:14419–14423), and L6 myoblasts (Mohammadi et al., 1992, Nature 358:684–684) expressing FGFR1 were previously described. HER14 cells are NIH 3T3 cells that overexpress the human EGF-receptor (EGFR) (Honegger et al., 1987, Cell 51:199–209)

Antibodies and GST-fusion proteins: Anti-Grb2 (N-SH3 domain), anti-Sosl, antiphosphotyrosine (anti-pY), anti-Shc, and anti-FGFR were previously described (Lowenstein et al., 1992, Cell 70:431–442; Spivak-Kroizman et al., 1994, J. Biol. Chem. 269:14419–14423). Anti-EGFR (Honegger et al., 1987, Cell 51:199–209) and anti-GST (Batzer et al., 1994, Mol. Cell. Biol. 14:5192–5201) antibodies were also previously described. Anti-FRS2 antibodies were generated against a GST fusion protein containing the C-terminal portion of the protein (amino acids 400–508 of FRS2). A GST fusion protein of Grb2, as well as fusion proteins of several Grb2 mutants, GST-Grb2-SH2, GST-Grb2(P49L), GSTGrb2 FLVR (R86K), (Lowenstein et al., 1992, Cell 70:431–442; Clark et al., 1992, Nature 356:340–344; Skolnik et al., 1993, Science 260:1953–1955) were generated as previously described.

Immunoprecipitation and immunoblotting analysis: Transfected cells expressing either FGFR1 or EGFR were starved overnight: L6 cells in growth medium containing 0.5% fetal calf serum (FCS), and PC12 cells in medium containing 0.5% FCS and 0.5% horse serum. Starved cells were treated with 5 nM aFGF together with 5 µg/ml heparin, or with 16 nM EGF, and were incubated at 37° C. for 5 minutes, or for the indicated times. The cells were lysed and subjected to immunoprecipitation and immunoblotting analysis as previously described (Spivak-Kroizman et al., 1994, J. Biol. Chem. 269:14419–14423).

Purification of FRS2: FRS2 was purified from NIH 3T3 cells that had been stimulated as previously described (Spivak-Kroizman et al., 1994, J. Biol. Chem. 269:14419–14423) with aFGF and heparin. Cells were lysed, and the lysate was mixed with a Grb2-SH2 Affigel-10 column (10 mg SH2 protein was cross linked to 1 ml Affigel 10, Bio-Rad) for 3 hours at 4° C. The column was washed three times with HNTG (20 mM Hepes, 150 mM NaCl, 1% Triton X-100, 10% glycerol), and proteins were eluted with 10 mM Tris (pH 7.5) containing 1% SDS and 2.5% (v/v) β mercaptoethanol. The column was incubated with the elution buffer for 10 min. at 100° C. The eluate was next diluted 50 fold with HNTG and the diluted protein was mixed with affinity-purified antiphosphotyrosine antibodies (anti-P-Tyr) bound to protein-A sepharose for 5 hours at 4° C. FRS2 was eluted from the antibody column with 100 mM phenylphosphate in 10 mM Tris pH 7.5. The sample was then applied to an 8% SDS gel, transferred to a nitrocellulose filter and visualized by staining with Ponceau S.

Protein sequencing: The band corresponding to FRS2 was excised from the nitrocellulose filter. The nitrocellulose was cut into 2 cm square pieces, wetted with methanol, then reduced with 200 ul of 10 mM DTT, 200 mM Tris pH 9.2, 5 mM EDTA at 50° C. for one hour and alkylated by the addition of 1/10 volume of 250 mM 4-vinyl pyridine in acetonitrile for 30 min. at room temperature. The nitrocellulose was then washed five times with 10% acetonitrile in water, 50 µl of 100 mM Tris pH 8.2, 1% octylglucoside, 10% acetonitrile containing 200 ng of modified porcine trypsin (Promega) was then added, and the sample was incubated 18 hrs at 37° C. with constant shaking. The supernatant containing peptides released from the nitrocellulose was injected directly onto reversed phase HPLC for peptide separation. A 1×150 mm Reliasil C-18 column was used in a Michrom HPLC. Solvents were A=0.1% TFA in acetonitrile/water (3:97), B=0.9% acetonitrile/water (97:3). The column was washed with 5% B until a flat baseline is obtained, and was then eluted with a 5 to 65% B gradient over 60 minutes. Monitoring was at 214 nm, peaks were collected into a deep well polypropylene microliter plate and stored frozen. Sequencing was performed with an Applied Biosystems 494 using standard reagents and programs from the manufacturer.

cDNA cloning of FRS2: A pair of degenerate primers was synthesized based upon the amino acid sequence of tryptic peptide #2 (VYENINGLSIPSASGV). PCR was performed with these two primers using cDNA prepared from mRNA isolated from 3T3 cells. The 60 base pair long product of this reaction was sequenced and found to have the correct amino acid sequence. A second round of PCR was then performed with the same cDNA using one primer chosen from the sequence of the initial 60 bp reaction product, and a second degenerate primer based upon the sequence of tryptic peptide #1 of FRS2 (FVLGPTPVQK); this reaction gave a 170 base pair product. A third round of PCR was performed with one primer from this 170 base pair product and a T3 primer from the Bluescript vector. The 1.2 kb product of this reaction contained the sequence of peptide #1. Finally, the 1.2 kb fragment was used as a probe for screening a λ cDNA library generated from Swiss 3T3 cells (Stratagene). Two phage clones of λp90-1 and λp90-2 were isolated and further analyzed. Determination of the deduced amino acid sequences of these two clones revealed a long open reading frame (ORF) that contained the sequences of the four tryptic peptides that were isolated from purified FRS2.

Transient expression in 293 cells: 293 cells were grown to 70% confluency on 10 cm tissue culture dishes. Cells were transiently transfected with various expression vectors (as indicated in the figures) using the lipofectamine reagent (Gibco BRL). Empty expression vectors were used to adjust the amount of DNA transfected to each plate to a constant of 10 µg.

[$^3$H] myristic acid labeling: Subconfluent 293 cells were transfected with wild tp FRS2 or the G2A mutant; 36 hours after transfection, cells were washed twice with DMEM supplemented with 2% dialysed FCS and were incubated for 3 hours at 37° C. in the same medium to which 100 µCi/mL [$^3$H] myristic acid (Amersham) was added. Cells were then lysed and immunoprecipitated with anti-FRS2 antibodies. The immunoprecipitates were separated by 8% SDS-PAGE, and the gel was treated with an ENTENSIFY solution (Dupont) according to the manufacture's protocol. The gel was dried and analyzed by autoradiography. As a control for normalizing the amount of protein loaded, a 10% of each immunoprecipitate was transferred to a nitrocellulose filter and immunoblotted with anti-FRS2 antibodies.

Immunofluorescence analysis: HeLa cells were transiently transfected with the HA-tagged construct of FRS2 or its G2A mutant. 24–48 hours after transfection the cells were plated on glass cover-slips coated with poly-L-lysine. 16 hours later, the cells were fixed with 4% paraformaldehyde in PBS and permeabilized with 0.2% Triton X-100 in PBS for 20 minutes at room temperature. Cells were treated with a blocking solution that contain 5% goat serum and 5% horse serum (Vector Laboratories, CA), stained with anti HA-antibody and secondary fluorescein-conjugated goat anti-mouse antibodies.

Generation of PC12 cells stably expressing FRS2: FRS2 cDNA was cloned into the LXSN expression vector, and a high titer stock of virus was produced as previously described. Rozakis-Adcock et al., 1992, Nature 360:689–692. Parental cells were infected with a virus that combined wild type FRS2 and the neomycin resistant gene and were selected for one week in medium supplemented with Geneticin (500 µg/ml). PC12 cells that express Ras (N17) were infected with FRS2 expression virus which contain histidinol dehydrogenase as a selection marker. Cells were then selected with histidinol (800 µg/ml) for two weeks. Pools of selected cultures were used in the studies. Expression of Ras (NI7) was induced by overnight treatment with 2 µM dexamethasone.

Analysis of PC 12 cells differentiation: PC12 cells infected with an FRS2 virus were seeded at a density of $10^5$ cells per 60 mm tissue culture dish. Cells were grown in DMEM containing 10% fetal calf serum and 10% horse serum for 24 hours. The medium was supplemented with aFGF (2.5 nM) and heparin (5 µg/ml) for an additional 48 hours. PC12 cells that coexpress FRS2 and Ras (N17) were treated in addition with 2 µM dexamethasone. Neurite outgrowth was quantitated by scoring random groups of 200 cells for the length of their neurites and determining the average length per cell for every treatment.

Example 1
SH2 Domain of Grb2 Binds to FRS2

Grb-2 contains one SH2 domain flanked by two SH3 domains. Lowenstein et al., 1992, Cell 70:431–442. Since tyrosine phosphorylated FRS2 binds to Grb2, its ability to interact with the SH2 domain alone was tested. A glutathione-S-transferase (GST)-fusion protein of the Grb2 SH2 domain was used to precipitate associating proteins from lysates of FGF-stimulated cells. Analysis with anti-pY antibodies showed that both, tyrosine-phosphorylated Shc and FRS2 were associated with the Grb2 SH2 domain in an FGF-dependent manner. By contrast, a GST fusion protein with a mutated, binding-defective form of the Grb2 SH2 (R86K) failed to precipitate either protein.

The far-Western technique was applied to determine whether the interaction between FRS2 and the SH2 domain of Grb2 was direct. Lysates from FGF-stimulated or unstimulated cells were immunoprecipitated with either anti-Grb2 or anti-pY antibodies, and analyzed by blotting with GST (as a control), GST-Grb2, or GST-Grb2 (P49L), a point mutant in the N-terminal SH3 domain corresponding to the Sem-5 loss-of-function allele (Clark et al., 1992, Nature 359:340–344. Both GST-Grb2 and the form with the mutated SH3 domain bound directly to tyrosine-phosphorylated FRS2 (data not shown), providing further confirmation of a direct interaction involving the Grb2 SH2 domain.

Example 2
Grb2/FRS2 Complex is Bound to Sos in FGF-Stimulated Cells

Grb2 binds to the guanine-nucleotide releasing factor Sos1 through its two SH3 domains. Schlessinger, 1994, Curr. Opin. Gen. Dev. Biol. 4:25–30. Experiments were performed to determine whether the complex formed between FRS2 and Grb2 also interacts with Sos1. Lysates of aFGF-stimulated or unstimulated cells were immunoprecipitated with antibodies against FGFR1, Grb2, or Sos1. The immunoprecipitates were separated by SDS-PAGE, and immunoblotted with anti-phosphotyrosine antibodies. Tyrosine-phosphorylated FRS2 was seen to be associated with both Grb2 and Sos1 in FGF-stimulated cells, but was not detected in anti-FGFR1 (or anti-Shc) immunoprecipitates. This experiment indicated that a ternary complex, composed of Grb2, Sos1 and FRS2 was formed in response to aFGF stimulation. Far-western blotting experiments also confirmed the existence of a complex containing FRS2, Grb2, and Sos1. The experiments suggested that association between Grb2 and FRS2 was mediated by the SH2 domain of Grb2, and was dependent upon FGF stimulation. The association between Sos1 and Grb2 was constitutive and mediated by the SH3 domains.

Example 3
Purification of FRS2

The experiments in Example 1 showed that the SH2 domain of Grb2 binds to tyrosine phosphorylated FRS2. This information was used to develop an affinity chromatography method for the purification of FRS2. NIH 3T3 cells were stimulated with aFGF, lysed, and the cell lysate was applied to an affigel affinity matrix containing immobilized Grb2 SH2 domain. The tyrosine phosphorylated FRS2 bound the SH2 affigel matrix and was released from the matrix by boiling in the presence of SDS and reducing agents. The FRS2 containing sample was then subjected to a second affinity chromatography purification step using anti-phosphotyrosine antibodies. Tyrosine phosphorylated FRS2 was bound to anti-phosphotyrosine antibodies, and the complex was applied to a protein A-sepharose column. Phosphorylated FRS2 was then released from the column using 100 mM phenyl phosphate.

The eluted protein was analyzed by SDS-PAGE. After transfer to nitrocellulose, Ponceau-S staining revealed a doublet of apparent molecular weight of 92/95 kDa, corresponding to FRS2. The purified FRS2 protein band was excised from the filter, digested with trypsin, and the tryptic peptides were resolved by reverse phase HPLC. The amino acid sequences of four tryptic peptides were determined using a solid phase microsequencer.

Example 4
cDNA Cloning of FRS2

Peptide sequences from FRS2 were used to design oligonucleotides for amplification by polymerase chain reaction (PCR) of cDNA prepared from mRNA isolated from NIH-3T3 cells. A 1.2 kb PCR product contained the sequences of proteolytic peptide #1 (FVLGPTPVQK) and peptide #2 (VYENINGLSIPSASGV) from FRS2. The 1.2 kb PCR product was then used as a probe for screening a cDNA library from NIH-3T3 cells. Two overlapping clones, λp90-1 and λp90-2, were isolated. Determination of the nucleotide sequences of the two clones demonstrated that λp90-2 contained the sequences of all four tryptic peptides isolated from FRS2 and that λp90-2 represents a full-length cDNA clone of FRS2.

The deduced amino acid sequence of FRS2 determined from clone λp90-2 is presented in FIG. 1A. The coding sequence of FRS2 begins at nucleotide number 308. The first methionine is within a Kozak consensus sequence, and is followed by an open reading frame (ORF) of 1527 base pairs, ending with a stop codon at nucleotide 1834. This ORF encodes a protein containing 508 amino acids with a predicated molecular mass of 56800 daltons. The sequence of FRS2 contains a consensus myristylation sequence (MGXXXS/T) at the amino terminus of the molecule MGSCCS. Resh, 1994, Cell 76:411–413. In addition, FRS2 contains a stretch of 120 amino acids (residues 11 to 139) with 29% sequence identity to the PTB (phosphotyrosine binding) domain of IRS1 (FIG. 1B). Sun et al., 1991, Nature 352:7377. It has been shown that the PTB domain of IRS1 binds to a tyrosine-phosphorylated NPXYp sequence in the juxtamembrane region of the insulin receptor. White et al., 1988, Cell 54:641–649. FRS2 also contains two potential Grb2 binding sites (NYEN and NYVN) (FIG. 1B).

The tissue expression pattern of FRS2 were examined by Northern blot analysis of mRNA isolated from adult mouse tissues. FRS2 was ubiquitously expressed and most abundant in brain, kidney, lung, ovary and testis. Polyclonal antibodies were raised in rabbits against a C-terminal portion of FRS2 expressed in *E.coli* as a GST fusion protein to characterize the FRS2 protein. The anti-FRS2 antibodies precipitated a protein from NIH-3T3 cells as well as from PC12 cells that migrates in SDS-PAGE as a doublet of 92–95 kDa. The discrepancy between the predicted molecular weight of FRS2 (56,800 daltons) versus its migration in SDS gels may result in part from post-translational modifications.

The association between Grb2 and FRS2 in lysates from NIH-3T3 cells using anti-FRS2 antibodies were also examined. NIH-3T3 cells were stimulated with aFGF, and lysates prepared from unstimulated or stimulated cells were then subjected to immunoprecipitation with antibodies against Grb2, FRS2, Sos1, Shc or FGFR1, followed by immunoblotting with several different antibodies. This experiment showed ligand-dependent association of Grb2 with tyrosine phosphorylated FRS2 in aFGF stimulated cells. Similarly, Sos1 was found to be associated with FRS2 only in aFGF-stimulated cells. Interestingly, more pronounced co-immunoprecipitation of Grb2 and Sos1 was detected in lysates of aFGF stimulated cells, suggesting that the interaction between Grb2 and tyrosine phosphorylated FRS2 may stabilize complex formation between Grb2 and Sos1.

Association between FRS2 and FGFR1 or between FRS2 and Shc in FGF-stimulated or unstimulated cells was not detected. Similarly, the association between FRS2 and other signaling molecules such as Nck, phospholipase Cλ, or p85, the regulatory subunit of PI-3 kinases were also not detected. Taken together, these experiments demonstrate that aFGF stimulation leads to tyrosine phosphorylation of FRS2, which in turn binds to Grb2/Sos1 forming an FGF-dependent ternary complex.

Example 5
FRS2 is Myristylated and Targeted to the Cell Membrane

The amino terminus of FRS2 contains a putative myristylation sequence followed by a phosphotyrosine binding domain (PTB domain) similar to the PTB domain of IRS1. Resh, 1994, Cell 76:411–413. The role of the putative myristylation sequence was examined by generation of a point mutant (G2A) in which a key glycine residue in the consensus sequence was replaced by alanine. Expression vectors that directed the synthesis of wild type FRS2 or the mutant G2A were transiently expressed in human 293 cells. The transfected cells were labeled with [$^3$H] myristic acid, lysed, subjected to immunoprecipitation with anti-FRS2 antibodies, and analyzed by 8% SDS-PAGE and autoradiography. Incorporation of [$^3$H] myristic acid could be detected in wild type FRS2 but not in the G2A point mutant.

The cellular distribution of FRS2 was analyzed in transfected cells. HeLa cells were transiently transfected with an expression vector that directs the synthesis of an HA-tagged form of wild type FRS2 or the point mutant (G2A). Transfected cells were permeabilized and labeled with fluorescein labeled anti-HA antibodies. Visualization by confocal fluorescence microscopy demonstrated that, while wild type FRS2 was primarily associated with the cell membrane, the G2A mutant was distributed throughout the cytoplasm. This experiment demonstrated that wild type FRS2 was targeted to the cell membrane and that myristylation was required for this localization.

A cellular fractionation procedure was used to study the distribution of wild type FRS2 and the G2A mutant. Particulate and soluble fractions were prepared from untreated or aFGF-treated cells and FRS2 was immunoprecipitated from both cellular fractions. FGFR1 was used as a marker to ascertain that the fractionation protocol correctly separated cytosolic from membrane bound proteins. FGFR1 was identified exclusively in the particulate fraction and was phosphorylated on tyrosine residues in aFGF stimulated cells. Endogenous FRS2 was found to be associated exclusively with the particulate fraction, and aFGF stimulation led to tyrosine phosphorylation of FRS2 and binding to Grb2. By contrast, the non-myristylated mutant (G2A) of FRS2 was found in the soluble fraction and was not tyrosine phosphorylated in FGF stimulated cells. The electrophoretic mobility of the non-myristylated form was altered in FGF-stimulated cells, suggesting that aFGF may induce Ser/Thr phosphorylation of the mutant FRS2 protein. The studies show that FRS2 was myristylated, and that myristylation was essential for its targeting to the cell membrane, for tyrosine phosphorylation of FRS2 and for recruitment of Grb2.

Example 6
Activation of the MAPK Pathway by Overexpression of FRS2

The ability of FRS2 to recruit Grb2 to the cell membrane in response to aFGF stimulation raised the possibility that its physiological role is to link FGF receptor activation to the Ras/MAP kinase signaling pathway. To explore this possibility, increasing concentrations of FRS2 was transiently overexpressed together with expression of a constant amount of the FGF receptor and an HA-tagged ERK1, in 293 cells. The activity of ERK1 was measured in an immunocomplex assay (Dikic et al., 1996, J. Biol. Chem. 270:15125–15129) using myelin basic protein (MBP) as a substrate. Overexpression of FRS2 lead to a proportional increase in tyrosine phosphorylation of MAP kinase and phosphorylation of MBP.

While overexpression of wild type FRS2 led to strong activation of MAP kinase, overexpression of the non-myristylated mutant led to a drastically reduced MAP kinase activation. MAP kinase activation induced by overexpression of the non-myristylated mutant was reduced by nearly 70% as compared to activation of MAP kinase induced by overexpression of wild type FRS2, after subtraction of the background activation induced by endogenous FRS2 molecules that are expressed in these cells. Unlike wild-type FRS2 which was tyrosine phosphorylated and hence bound to Grb2, the non-myristylated FRS2 mutant was not tyrosine phosphorylated in response to FGFR activation.

To examine the role of Ras in this process the effect of FRS2 overexpression on MAP kinase activity was analyzed in the presence of a dominant interfering mutant of Ras (N17). This experiment showed that expression of the dominant interfering mutant of Ras efficiently blocked FRS2-induced MAP kinase activation. However, the tyrosine phosphorylation of FRS2 and its association with Grb2 were not affected by the expression of the dominant interfering Ras(N17) mutant. These experiments therefore demonstrated that FRS2 functioned as a link between activated FGF receptors and the Ras/MAP kinase cascade, and that FRS2 acted upstream of Ras in this pathway.

Example 7
Overexpresion of FRS2 Promotes Neurite Outgrowth in PC12 Cells

PC12 cells were stably transfected with expression vectors that directed the synthesis of either wild type FRS2 or the non-myristylated G2A mutant. The cells were incubated with a low concentration of aFGF and heparin that induced weak, barely detectable, neurite outgrowth in the parental PC12 cells. The experiment demonstrated that overexpression of FRS2 led to strong potentiation of aFGF-induced neurite outgrowth in these PC12 cells. By contrast, expression of the non-myristylated FRS2 mutant did not influence aFGF-induced neurite outgrowth in the transfected cells.

It was noteworthy that the PC12 cell line used in this study expressed endogenous FRS2 and low levels of endogenous FGF receptors. Therefore, aFGF-stimulation promoted flattening, adhesion, and weak neurite outgrowth of control cells. Immunoprecipition and immunoblotting experiments confirmed that endogenous and transfected wild type FRS2 were both tyrosine phosphorylated, while the non-myristylated FRS2 mutant is not tyrosine phosphorylated in response to aFGF stimulation.

The role of Ras in FRS2-induced neurite outgrowth was tested by conditional expression in PC12 cells of a dexamethasone-inducible dominant interfering mutant of Ras(N17). Overexpression of Ras(N17) affected neither the expression of FRS2 nor tyrosine phosphorylation of FRS2. However, FRS2-induced neurite outgrowth was totally blocked by overexpression of Ras(N17), indicating that it is dependent upon Ras activation.

Although certain embodiments and examples have been used to describe the present invention, it will be apparent to those skilled in the art that changes to the embodiments and examples shown may be made without departing from the scope or spirit of the invention.

Those references not previously incorporated herein by reference, including both patent and non-patent references, are expressly incorporated herein by reference for all purposes.

Other embodiments are encompassed by the following claims.

What is claimed is:

1. An isolated, enriched or purified polypeptide, comprising the amino acid sequence set forth in SEQ ID NO:9.

2. An isolated, enriched, or purified polypeptide, wherein said polypeptide comprises at least 100 contiguous amino acid residues of the amino acid sequence set forth in SEQ ID NO:9.

3. The polypeptide according to claim 2, wherein said polypeptide comprises at least 141 contiguous amino acid residues of the amino acid sequence set forth in SEQ ID NO:9.

4. The polypeptide according to claim 2, wherein said polypeptide comprises at least 200 contiguous amino acid residues of the amino acid sequence set forth in SEQ ID NO:9.

5. The polypeptide according to claim 2, further comprising a second polypeptide, said second polypeptide fused to said polypeptide.

6. The polypeptide according to claim 5, wherein said second polypeptide is at least one selected from the group consisting of glutathione-S-transferase, hemagglutinin, and maltose-binding protein, or a fragment of any one of said second polypeptides.

7. An isolated, enriched or purified polypeptide, comprising an amino acid sequence that:

(a) differs from the sequence set forth in SEQ ID NO:9 in that it lacks at least one, but not all, of the following segments of amino acid residues: 1–10, 11–152 or 153–508; or (b) has the amino acid sequence set forth from amino acid residues 1–10, 11–152 or 153–508 of SEQ ID NO:9.

8. An isolated, enriched or purified polypeptide, comprising an amino acid sequence that differs from the sequence set forth in SEQ ID NO:9 in that it lacks at least one, but not all, of the domains selected from the group consisting of a myristylation region, a phosphotyrosine binding domain and a C-terminal region.

9. The polypeptide according to claim 7 or claim 8, further comprising a second polypeptide, wherein said second polypeptide is fused to said amino acid sequence.

10. The polypeptide according to claim 9, wherein said second polypeptide is at least one selected from the group consisting of glutathione-S-transferase, hemagglutinin, and maltose-binding protein, or a fragment of any one of said polypeptides.

* * * * *

SEQUENCE LISTING (1) GENERAL INFORMATION:

(iii) NUMBER OF SEQUENCES:  11

(2) INFORMATION FOR SEQ ID NO: 1:

(i) SEQUENCE CHARACTERISTICS:
      (A) LENGTH:       10 amino acids
      (B) TYPE:         amino acid
      (C) STRANDEDNESS: single
      (D) TOPOLOGY:     linear (ii) MOLECULE TYPE:     peptide (xi) SEQUENCE DESCRIPTION: SEQ ID NO: 1:

```
Phe Val Leu Gly Pro Thr Pro Val Gln Lys
 1               5                  10
```

(2) INFORMATION FOR SEQ ID NO: 2:

(i) SEQUENCE CHARACTERISTICS:
      (A) LENGTH:       16 amino acids
      (B) TYPE:         amino acid
      (C) STRANDEDNESS: single
      (D) TOPOLOGY:     linear (ii) MOLECULE TYPE:     peptide (xi) SEQUENCE DESCRIPTION: SEQ ID NO: 2:

```
Val Tyr Glu Asn Ile Asn Gly Leu Ser Ile Pro Ser Ala Ser Gly Val
 1               5                  10                  15
```

(2) INFORMATION FOR SEQ ID NO: 3:

(i) SEQUENCE CHARACTERISTICS:
      (A) LENGTH:       6 amino acids
      (B) TYPE:         amino acid
      (C) STRANDEDNESS: single
      (D) TOPOLOGY:     linear (ii) MOLECULE TYPE:     peptide (ix) FEATURE:
      (D) OTHER INFORMATION:  "Xaa" stands for any amino acid.

(xi) SEQUENCE DESCRIPTION: SEQ ID NO: 3:

```
Met Gly Xaa Xaa Xaa Ser
 1               5
```

(2) INFORMATION FOR SEQ ID NO: 4:

(i) SEQUENCE CHARACTERISTICS:
      (A) LENGTH:       6 amino acids
      (B) TYPE:         amino acid
      (C) STRANDEDNESS: single
      (D) TOPOLOGY:     linear (ii) MOLECULE TYPE:     peptide (ix) FEATURE:
      (D) OTHER INFORMATION:  "Xaa" stands for any amino acid.

(xi) SEQUENCE DESCRIPTION: SEQ ID NO: 4:

```
Met Gly Xaa Xaa Xaa Thr
 1               5
```

(2) INFORMATION FOR SEQ ID NO: 5:

```
            (i) SEQUENCE CHARACTERISTICS:
                (A) LENGTH:              6 amino acids
                (B) TYPE:                amino acid
                (C) STRANDEDNESS:        single
                (D) TOPOLOGY:            linear (ii) MOLECULE TYPE:           peptide (xi) SEQUENCE DESCRIPTION: SEQ ID NO: 5:

Met Gly Ser Cys Cys Ser
 1               5

(2) INFORMATION FOR SEQ ID NO: 6:

(i) SEQUENCE CHARACTERISTICS:
                (A) LENGTH:              4 amino acids
                (B) TYPE:                amino acid
                (C) STRANDEDNESS:        single
                (D) TOPOLOGY:            linear (ii) MOLECULE TYPE:           peptide (xi) SEQUENCE DESCRIPTION: SEQ ID NO: 6:

Asn Pro Xaa Tyr
 1

(2) INFORMATION FOR SEQ ID NO: 7:

(i) SEQUENCE CHARACTERISTICS:
                (A) LENGTH:              4 amino acids
                (B) TYPE:                amino acid
                (C) STRANDEDNESS:        single
                (D) TOPOLOGY:            linear (ii) MOLECULE TYPE:           peptide (xi) SEQUENCE DESCRIPTION: SEQ ID NO: 7:

Asn Tyr Glu Asn
 1

(2) INFORMATION FOR SEQ ID NO: 8:

(i) SEQUENCE CHARACTERISTICS:
                (A) LENGTH:              4 amino acids
                (B) TYPE:                amino acid
                (C) STRANDEDNESS:        single
                (D) TOPOLOGY:            linear (ii) MOLECULE TYPE:           peptide (xi) SEQUENCE DESCRIPTION: SEQ ID NO: 8:

Asn Tyr Val Asn
 1

(2) INFORMATION FOR SEQ ID NO: 9:

(i) SEQUENCE CHARACTERISTICS:
                (A) LENGTH:              508 amino acids
                (B) TYPE:                amino acid
                (C) STRANDEDNESS:        single
                (D) TOPOLOGY:            linear (ii) MOLECULE TYPE:           protein (xi) SEQUENCE DESCRIPTION: SEQ ID NO: 9:

Met Gly Ser Cys Cys Ser Cys Pro Asp Lys Asp Thr Val Pro Asp Asn
 1               5                  10                  15

His Arg Asn Lys Phe Lys Val Ile Asn Val Asp Asp Asp Gly Asn Glu
```

-continued

```
                    20                  25                  30
Leu Gly Ser Gly Val Met Glu Leu Thr Asp Thr Glu Leu Ile Leu Tyr
                35                  40                  45
Thr Arg Lys Arg Asp Ser Val Lys Trp His Tyr Leu Cys Leu Arg Arg
 50                  55                  60
Tyr Gly Tyr Asp Ser Asn Leu Phe Ser Phe Glu Ser Gly Arg Arg Cys
 65                  70                  75                  80
Gln Thr Gly Gln Gly Ile Phe Ala Phe Lys Cys Ala Arg Ala Glu Glu
                 85                  90                  95
Leu Phe Asn Met Leu Gln Glu Ile Met Gln Asn Asn Ser Ile Asn Val
                100                 105                 110
Val Glu Glu Pro Val Val Glu Arg Ser Ser His Gln Thr Glu Leu Glu
            115                 120                 125
Val Pro Arg Thr Pro Arg Thr Pro Thr Thr Pro Gly Leu Gly Ala Gln
130                 135                 140
Asn Leu Pro Asn Gly Tyr Pro Arg Tyr Pro Ser Phe Gly Asp Ala Ser
145                 150                 155                 160
Ser His Pro Ser Ser Arg His Pro Ser Val Gly Ser Ala Arg Leu Pro
                165                 170                 175
Ser Val Gly Glu Glu Ser Thr His Pro Leu Leu Val Ala Glu Glu Gln
                180                 185                 190
Val His Thr Tyr Val Asn Thr Thr Gly Val Gln Glu Glu Arg Lys Asn
            195                 200                 205
Arg Ala Ser Val His Val Pro Pro Glu Ala Arg Val Ser Asn Ala Glu
            210                 215                 220
Ser Asn Thr Pro Lys Glu Glu Pro Ser Asn Pro Glu Asp Arg Asp Pro
225                 230                 235                 240
Gln Val Leu Leu Lys Pro Glu Gly Val Arg Phe Val Leu Gly Pro Thr
                245                 250                 255
Pro Val Gln Lys Gln Leu Met Glu Lys Glu Lys Leu Glu Gln Leu Gly
            260                 265                 270
Lys Asp Pro Val Ser Gly Ser Gly Ala Gly Asn Thr Glu Trp Asp Thr
            275                 280                 285
Gly Tyr Asp Ser Asp Glu Arg Arg Asp Val Pro Pro Val Asn Lys Leu
290                 295                 300
Val Tyr Glu Asn Ile Asn Gly Leu Ser Ile Pro Ser Ala Ser Gly Val
305                 310                 315                 320
Arg Arg Gly Arg Leu Thr Ser Thr Ser Thr Ser Asp Thr Gln Asn Ile
                325                 330                 335
Asn Asn Ser Ala Gln Arg Arg Pro Ala Leu Leu Asn Tyr Glu Asn Leu
            340                 345                 350
Pro Ser Leu Pro Pro Val Trp Glu Ala Arg Lys Leu Ser Arg Asp Glu
            355                 360                 365
Asp Asp Asn Leu Gly Pro Lys Thr Pro Ser Leu Asn Gly Tyr His Asn
370                 375                 380
Asn Leu Asp Pro Met His Asn Tyr Val Asn Thr Glu Asn Val Thr Val
385                 390                 395                 400
Pro Ala Ser Ala His Lys Ile Asp Tyr Ser Lys Arg Arg Asp Cys Thr
                405                 410                 415
Pro Thr Val Phe Asn Phe Asp Ile Arg Arg Pro Ser Leu Glu His Arg
                420                 425                 430
Gln Leu Asn Tyr Ile Gln Val Asp Leu Glu Gly Gly Ser Asp Ser Asp
            435                 440                 445
```

```
Asn Pro Gln Thr Pro Lys Thr Pro Thr Thr Pro Leu Pro Gln Thr Pro
            450                 455                 460

Thr Arg Arg Thr Glu Leu Tyr Ala Val Ile Asp Ile Glu Arg Thr Ala
465                 470                 475                 480

Ala Met Ser Asn Leu Gln Lys Ala Leu Pro Arg Asp Asp Gly Thr Ser
            485                 490                 495

Arg Lys Thr Arg His Asn Ser Thr Asp Leu Pro Met
            500                 505
```

(2) INFORMATION FOR SEQ ID NO: 10:

(i) SEQUENCE CHARACTERISTICS:
        (A) LENGTH: 112 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 10:

```
Asp Thr Gly Pro Gly Pro Ala Phe Lys Glu Val Trp Gln Val Ile Leu
1               5                   10                  15

Lys Pro Lys Gly Leu Gly Gln Thr Lys Asn Leu Ile Gly Ile Tyr Arg
            20                  25                  30

Leu Cys Leu Thr Ser Lys Thr Ile Ser Phe Val Lys Leu Asn Ser Glu
            35                  40                  45

Ala Ala Ala Val Val Leu Leu Met Asn Ile Arg Arg Cys Gly His Ser
50                  55                  60

Glu Asn Phe Phe Phe Ile Glu Val Gly Arg Ser Ala Val Thr Gly Pro
65                  70                  75                  80

Gly Glu Phe Trp Met Val Asp Asp Ser Val Val Ala Gln Asn Met His
            85                  90                  95

Glu Thr Ile Leu Glu Ala Met Arg Ala Met Ser Asp Glu Phe Arg Pro
            100                 105                 110
```

(2) INFORMATION FOR SEQ ID NO: 11:

(i) SEQUENCE CHARACTERISTICS:
        (A) LENGTH: 129 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 11:

```
Asp Thr Val Pro Asp Asn His Arg Asn Lys Phe Lys Val Ile Asn Val
1               5                   10                  15

Asp Asp Asp Gly Asn Glu Leu Gly Ser Gly Val Met Glu Leu Thr Asp
            20                  25                  30

Thr Glu Leu Ile Leu Tyr Thr Arg Lys Arg Asp Ser Val Lys Trp His
            35                  40                  45

Tyr Leu Cys Leu Arg Arg Tyr Gly Tyr Asp Ser Asn Leu Phe Ser Phe
            50                  55                  60

Glu Ser Gly Arg Arg Cys Gln Thr Gly Gln Gly Ile Phe Ala Phe Lys
65                  70                  75                  80

Cys Ala Arg Ala Glu Glu Leu Phe Asn Met Leu Gln Glu Ile Met Gln
            85                  90                  95

Asn Asn Ser Ile Asn Val Val Glu Glu Pro Val Val Glu Arg Ser Ser
```

-continued

```
                100              105              110
His Gln Thr Glu Leu Glu Val Pro Arg Thr Pro Arg Thr Pro Thr Thr
            115              120              125
Pro
```